United States Patent
Michels et al.

(10) Patent No.: US 9,804,180 B2
(45) Date of Patent: Oct. 31, 2017

(54) INCUBATION DEVICE AND METHODS FOR AUTOMATIC MOVEMENT OF A REACTION VESSEL THEREIN FOR AN AUTOMATIC ANALYSIS APPARATUS

(71) Applicant: Siemens Healthcare Diagnostics Products GmbH, Marburg (DE)

(72) Inventors: Thorsten Michels, Gross-Gerau (DE); Holger Pufahl, Liederbach (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 184 days.

(21) Appl. No.: 14/856,536

(22) Filed: Sep. 16, 2015

(65) Prior Publication Data
US 2016/0077117 A1   Mar. 17, 2016

(30) Foreign Application Priority Data
Sep. 17, 2014  (EP) ..................... 14185080

(51) Int. Cl.
*G01N 35/00*   (2006.01)
*B01L 1/02*   (2006.01)

(52) U.S. Cl.
CPC .......... *G01N 35/0099* (2013.01); *B01L 1/025* (2013.01); *G01N 35/00* (2013.01); *G01N 2035/00356* (2013.01)

(58) Field of Classification Search
CPC .......... B01L 1/025; G01N 2035/00356; G01N 35/00; G01N 35/0099; G01N 35/02
USPC .......... 436/43, 47, 48, 164, 501; 422/63, 65, 422/82.05, 82.09; 435/4, 287.3, 288.7, 435/303.1
See application file for complete search history.

(56) References Cited

U.S. PATENT DOCUMENTS

| 4,011,048 A | 3/1977 | Johnson, Jr. et al. |
| 5,650,122 A | 7/1997 | Harris et al. |
| 5,882,594 A * | 3/1999 | Kawaguchi .......... G01N 35/025 422/63 |
| 2005/0220671 A1 * | 10/2005 | Stein .................. G01N 35/0092 422/67 |

FOREIGN PATENT DOCUMENTS

| DE | 2726323 C2 | 5/1987 |
| DE | 3736632 A1 | 5/1988 |
| JP | H01267936 | 10/1989 |
| WO | WO 02/066598 | 8/2002 |

\* cited by examiner

*Primary Examiner* — Maureen Wallenhorst
(74) *Attorney, Agent, or Firm* — Dugan & Dugan, PC

(57) ABSTRACT

An incubation device for an automatic analysis apparatus includes an incubation unit having a number of reception positions for reaction vessels, a first transfer arm having a gripping device for one or more reaction vessels, which is configured to move the gripping device into a first access region, a second transfer arm having a gripping device for one or more reaction vessels, which is configured to move the gripping device into a second access position. This allows a larger sample throughput of the automatic analysis apparatus with, at the same time, frictionless and reliable operation. To this end, the first and the second access regions do not overlap, and the incubation unit is mounted so that it can be moved in such a way that at least one of the reception positions reaches the first and the second access regions.

13 Claims, 2 Drawing Sheets

INCUBATION DEVICE AND METHODS FOR AUTOMATIC MOVEMENT OF A REACTION VESSEL THEREIN FOR AN AUTOMATIC ANALYSIS APPARATUS

CROSS REFERENCE TO RELATED APPLICATION

This claims priority to European Patent Application No. EP 14185080.0, filed Sep. 17, 2014, which is hereby incorporated by reference herein in its entirety for all purposes.

FIELD

The invention relates to an incubation device for an automatic analysis apparatus, which incubation device comprises an incubation unit having a number of reception positions for reaction vessels and at least two transfer arms, each with a gripping device for one or more reaction vessels.

BACKGROUND

Numerous detection and analysis methods for the determination of analytes in bodily fluid samples or other biological samples are nowadays carried out in an automated fashion in a large number in automatic analysis apparatuses, also so-called in-vitro diagnostic systems. To this end, such analysis apparatuses conventionally comprise corresponding analysis or measurement stations as well as a range of transport instruments, for example conveyor belts, transport carousels or transfer arms having gripping instruments for sample vessels, reagent containers and reaction vessels, and furthermore pipetting instruments for the transfer of liquids. The apparatuses furthermore comprise a control unit which, by means of corresponding software, is capable of substantially independently planning and executing the working steps for the desired analyses.

Many of the analysis methods used in such analysis apparatuses operating in an automated fashion are based on optical methods. The determination of clinically relevant parameters, for example the concentration or activity of an analyte, is often carried out by mixing a part of the sample with one or more test reagents in a reaction vessel, which may also be the measurement cell, so as to initiate a biological reaction or a specific binding reaction which causes a measurable change in an optical or other physical property of the reaction mixture.

Conventionally, a sample aliquot is taken from a sample vessel by means of an automatic pipetting instrument and transferred into a reaction vessel. A reaction mixture is prepared by addition of one or more reagents.

Inside the automatic analysis apparatus, the reaction vessels are then typically moved by transfer arms to the various analysis stations. These transfer arms comprise a gripping device for securely taking and depositing the reaction vessels and have an access region defined by the range of the movement mechanics (and optionally further restricted on the control or software side), in which the reaction vessels can be taken or deposited.

After the sample and the reagents have been combined in the reaction vessel, many detection reactions used for the analysis require a certain incubation time, which may last a few minutes. During this incubation time, the reagent components, for example enzymes, enzyme substrates or antibodies, react with the analyte to be detected. Since many detection reactions are temperature-dependent, the incubation of the reaction mixtures is generally carried out in an incubation unit which has a plurality of reception positions for temporary storage of the reaction vessels, in which case the walls of the reception positions may be kept at a predetermined controlled temperature by means of heating/cooling.

SUMMARY

The incubation unit is in this case arranged in an incubation device of the automatic analysis apparatus, which furthermore comprises at least one of the transfer arms described above for depositing reaction vessels into the reception positions and for taking reaction vessels from the reception positions of the incubation unit. The reactions vessels may be transferred with the aid of a transfer arm, for example in the empty state, from a reaction vessel stock into the incubation unit, or they may be transferred in the partially filled state, for example merely containing the sample liquid, from a corresponding station of the analysis apparatus into the incubation unit, or they may be transferred in the fully filled state, containing the complete reaction mixture, from a corresponding station of the analysis apparatus into the incubation unit. Furthermore, after the incubation time, the reaction vessels need to be transferred with the aid of a transfer arm into the measuring unit. If the throughput of the automatic analysis apparatus is intended to be increased, i.e., more samples are intended to be analyzed in a shorter time, then the incubation device may also comprise a plurality of transfer arms, i.e., at least a second transfer arm, which can access the incubation unit. In this case, however, the problem arises that under certain circumstances a collision of the transfer arms may occur, which absolutely has to be avoided in order to avoid damage and operational interruptions. It has been found that such collision avoidance is relatively elaborate to implement in software technology: the software control must always coordinate which of the transfer arms is currently in which position, and if appropriate move the respective transfer arm away so that another transfer arm can gain access.

It is therefore an object of the invention to provide an incubation device and a method for moving one or more reaction vessels in such an incubation device, which allow greater sample throughput of the automatic analysis apparatus with, at the same time, frictionless and reliable operation.

In relation to the incubation device, this object is achieved according to the invention in that two transfer arms for the transfer of reaction vessels into or out of the incubation unit are provided, the access regions of the two transfer arms not overlapping, i.e., being separate from one another, and the incubation unit being mounted so that it can be moved, for example on a delivery rail or a carriage, in such a way that at least one of the reception positions reaches the two access regions of the two transfer arms. In the event of an access request of a transfer arm, the incubation unit then moves, at least with the corresponding reception position to which access is intended, into the access region of the respectively accessing transfer arm. It has surprisingly been found that the extra mechanical outlay entailed by the displaceable incubation unit is more than compensated for by the considerable simplification of the control software, and is furthermore substantially more reliable.

The present invention therefore relates to an incubation device for an automatic analysis apparatus, the incubation device comprising:

an incubation unit having a number of reception positions for reaction vessels, a first transfer arm having a gripping device for one or more reaction vessels, which is configured in order to move the gripping device into a first access region, and wherein the first and the second access region do not overlap, and the incubation unit is mounted so that it can be moved in such a way that at least one of the reception positions reaches the first and the second access region.

In relation to the method for the automated movement of one or more reaction vessels, the object is achieved in that the first and the second access region do not overlap, and in the event of access of one of the transfer arms, the incubation unit is moved in such a way that at least one of the receptacles reaches the respective access region of the accessing transfer arm.

The present invention thus furthermore relates to a method for the automatic movement of one or more reaction vessels in an incubation device as described above, wherein the incubation unit is moved in such a way that at least one of the reception positions reaches the respective access region of the accessing transfer arm.

Advantageously, the incubation unit is mounted so that it can be moved in such a way that each of the reception positions reaches the first and the second access region. In other words, the movement capability of the incubation unit extends so far that each of the transfer arms can access each of the reception positions. This gives the greatest possible flexibility in terms of the automated working processes in the incubation device, since any reception positions for reaction vessels can be used for the incubation, without having to take into account a restricted range of the individual transfer arms.

The process can be simplified even further in that the incubation unit is mounted so that it can be moved in such a way that it reaches a first position, in which each of the reception positions lies in the first access region, and/or is mounted so that it can be moved in such a way that it reaches a second position, in which each of the reception positions lies in the second access region. With respect to the method, the incubation unit is in this case advantageously moved into a position in such a way that each of the receptacles reaches the respective access region of the accessing transfer arm.

In such a configuration, one transfer arm and its respective access region is assigned precisely one position of the incubation unit. In the event of an access request of a transfer arm, the incubation unit is moved into the position assigned to the accessing transfer arm, without in this case having to take into account which of the access positions of the incubation unit of the transfer arm is intended to be accessed. This simplifies the software-side control of the incubation unit, for which only one position per transfer arm is now respectively specified. The incubation unit moves between these positions, only one software-side access request of the accessing transfer arm to the incubation unit being necessary for the movement into the respective position.

In another advantageous configuration of the incubation device and of the method, the transfer arms are restricted in their movement in such a way that mutual contact is prevented. This may be done either on the software side or, more advantageously, by a technical hardware configuration such that contact is geometrically no longer possible. This may be done by mechanical limitation of the movement paths of the transfer arms. Such a measure prevents contact of the transfer arms particularly reliably, and ensures particularly reliable and unimpaired operation of the automatic analysis apparatus.

In one preferred embodiment of the incubation device according to the invention, the first and the second access region lie in the same horizontal plane, and the incubation unit is mounted so that it can be moved horizontally, for example on horizontal rails or on a carriage. With respect to the method according to the invention, the incubation unit is moved horizontally in this arrangement.

Preferably, the reception positions can be thermally regulated. To this end, the incubation unit comprises corresponding heating and/or cooling instruments.

The present invention furthermore relates to an automatic analysis apparatus which contains an incubation device as described above and therefore has particularly reliable and unimpaired operation.

A preferred automatic analysis apparatus comprises a first unit for measuring a first physical property of a reaction mixture and a second unit for measuring a second physical property of a reaction mixture, i.e., two measurement stations. Advantageously, the two measurement stations are respectively configured in order to measure at least one optical property of a reaction mixture. The first and the second unit for measuring a physical property of a reaction mixture may, for example, be selected from the group: photometer, nephelometer, turbidimeter and luminometer.

A "photometer" is intended to mean a measuring unit which comprises at least one light source and at least one light detector, which are configured in such a way that they make it possible to measure the absorbance of light of a particular wavelength in a sample or a reaction mixture. Typically, the wavelength of the light emitted by the light source is selected in such a way that it is absorbed by a substance to be detected in the sample, for example by a chromophore which is formed as a result of an analyte-dependent reaction in a reaction mixture.

A "turbidimeter" is intended to mean a measuring unit which comprises at least one light source and at least one light detector and is configured in such a way that it makes it possible to measure the absorbance of light in a sample or a reaction mixture. Typically, the wavelength of the light emitted by the light source is selected in such a way that it is absorbed by macromolecules to be detected in the sample, for example particle aggregates, which are formed as a result of an analyte-dependent reaction in a reaction mixture.

A "nephelometer" is intended to mean a measuring unit which comprises at least one light source and at least one light detector and is configured in such a way that it makes it possible to measure the absorbance of light in a sample or a reaction mixture. Typically, the arrangement of the light source and of the light detector is selected in such a way that the scattered light, which is scattered by macromolecules to be detected in the sample, for example particle aggregates, which are formed as a result of an analyte-dependent reaction in a reaction mixture, can be measured.

A "luminometer" is intended to mean a measuring unit which comprises at least one light detector, usually a photomultiier, and which is configured in such a way that it makes it possible to measure the emission of light from a sample or from a reaction mixture. Typically, the light detector is selected in such a way that bioluminescence, chemiluminescence and/or fluorescence which is emitted by a substance to be detected in the sample, for example by a luminescent or fluorescent signal group which is formed as a result of an analyte-dependent reaction in a reaction mixture, can thereby be measured.

The advantages achieved by the invention are, in particular, that contact of the transfer arms is avoided particularly easily on the software side by the separation of the access regions of the transfer arms in conjunction with an incubation unit which can be moved between the access regions. Reliable and unimpaired operation of the incubation device is thereby made possible, and a particularly high throughput of the automatic analysis apparatus can be achieved.

BRIEF DESCRIPTION OF THE DRAWINGS

The invention will be explained in more detail with the aid of a drawing, in which.

Parts which are the same are provided with the same references in all the figures.

DETAILED DESCRIPTION

Figure 1:
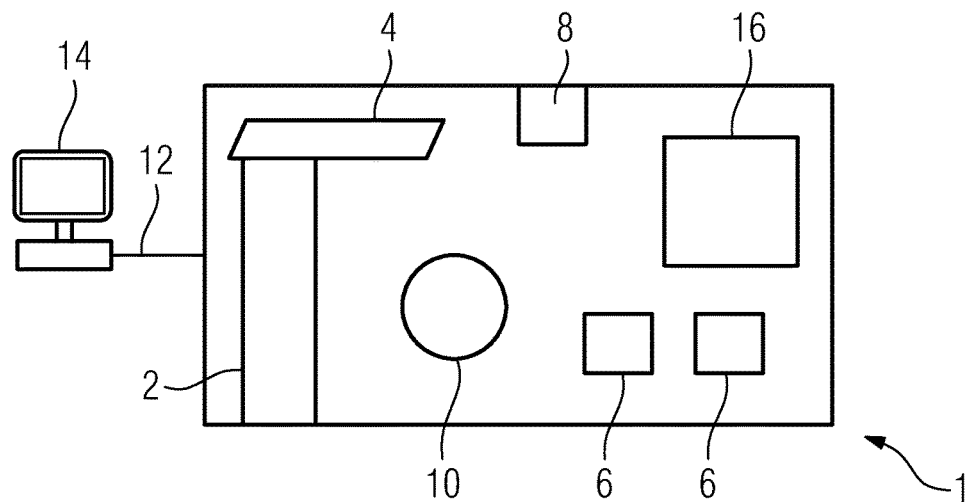
FIG. 1 shows a schematic representation of an automatic analysis apparatus.

FIG. 1 shows a schematic representation of an automatic analysis apparatus 1 with some components contained therein. In this case, only the most important components are represented in a very simplified way, in order to explain the basic function of the automatic analysis apparatus 1, without thereby representing the individual parts of each component in detail.

The automatic analysis apparatus 1 is configured in order to carry out a wide variety of analyses of blood or other bodily fluids fully automatically, without actions by a user being required for this. Rather, the latter are restricted to maintenance or repair and refilling work, for example when reaction vessels or reagents need to be refilled.

The samples are delivered to the automatic analysis apparatus 1 on carriages (not represented in detail) in a delivery rail 2. Information regarding the analyses to be carried out for each sample may in this case, for example, be communicated by means of barcodes applied on the sample vessels, which barcodes are read in the automatic analysis apparatus 1. Aliquots are taken from the sample vessels in a pipetting device 4 by means of a pipetting needle (not represented in detail).

The aliquots are likewise delivered to reaction vessels (not represented in detail), in which the actual analyses are carried out by means of a wide variety of measuring units 6, for example photometers, nephelometers, turbidimeters or luminometers, etc. The reaction vessels are taken from a reaction vessel store 8. In addition, further reagents which are required depending on the analysis to be carried out may be delivered from a reagent store 10 to the respective reaction vessel by means of a further pipetting needle (not represented).

The transport of the cuvettes inside the automatic analysis apparatus is carried out by transport devices (not represented in detail here), for example transfer arms, which can be moved in a wide variety of spatial directions and comprise a gripping device for taking the reaction vessels. The entire process is controlled by a control device, for example by a computer 14 connected via a data line 12, assisted by a multiplicity of further electronic circuits and microprocessors (not represented in detail) inside the automatic analysis apparatus 1 and its components.

After the sample and the reagents have been combined in the reaction vessel, many of detection reactions used for analysis are based on the measurement of particular properties of a resulting reaction product after a certain reaction time has elapsed. During this reaction time, particular enzymes, antibodies or the like react with the analytes to be determined. During the reaction time, the reaction vessels are in this case mounted in an incubation device 16 of the automatic analysis apparatus 1, which is schematically represented in more detail in FIG. 2 and FIG. 3.

Figure 2:
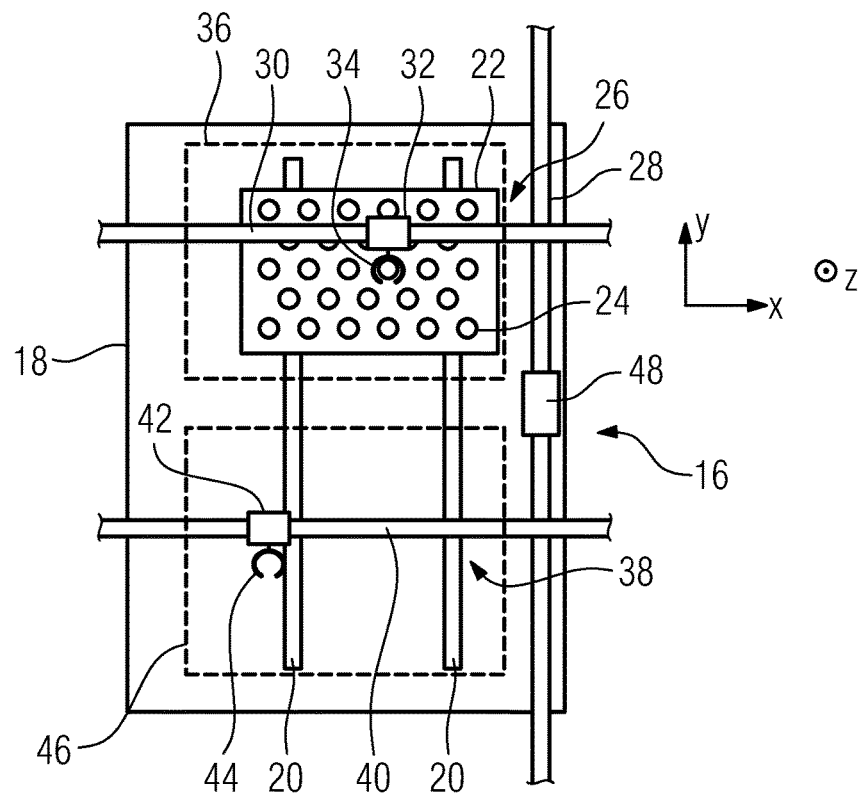
FIG. 2 shows a schematic representation of the incubation device of the automatic analysis apparatus in a plan view.
Figure 3:
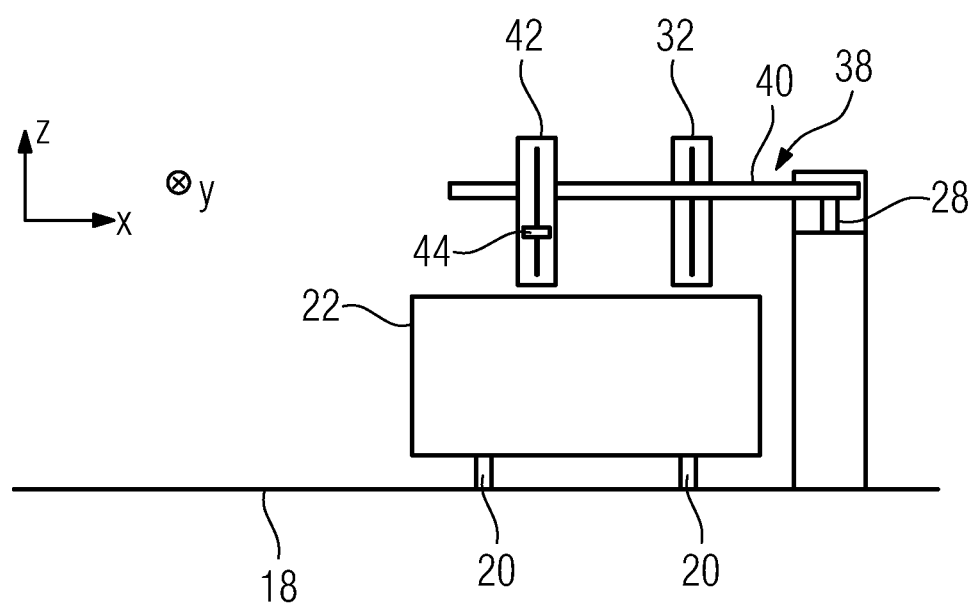
FIG. 3 shows a schematic representation of the incubation device in a front view.

The incubation device 16 is represented in a plan view in FIG. 2, and in a front view in FIG. 3. For the description of FIG. 2 and FIG. 3, spatial directions will be used below which are shown respectively adapted to the viewing direction in the two figures. In FIG. 2, the spatial direction x extends from left to right, the spatial direction y from the bottom upward and the spatial direction z out of the plane of the drawing. FIG. 3 is rotated in its view through 90 degrees about the x axis. In FIG. 3, therefore, because of the front view the spatial direction x again extends from left to right, the spatial direction y extends into the plane of the drawing and the spatial direction z extends from the bottom upward.

Arranged on the bottom 18 of the incubation device 16, there are two rails 20 arranged next to one another which extend straight in the spatial direction y over almost the entire extent of the incubation device 16. Arranged on the rails 20, there is an incubation unit 22 which is essentially configured as a rectangular block and can be moved by means of a drive (not represented in detail) along the rails 20 in the spatial direction y, i.e. horizontally.

Since a large number of detection reactions are dependent on the temperature, the incubation unit 22 has a plurality of reception positions 24 for temporary storage of the reaction vessels during the incubation time, and the walls of the reception positions can be kept at a predetermined controlled temperature by means of heating/cooling. The reception positions 24 are introduced as cylindrical openings on the opposite side of the incubation unit 22 from the rails 20 in a regular geometrical pattern. In this way, a multiplicity of reaction vessels can be mounted simultaneously. In FIG. 2, for reasons of clarity, only one of the identical reception positions 24 is provided with a reference.

The incubation device 16 furthermore comprises a first transfer arm 26. This is mounted on an elevated rail 28 extending in the spatial direction y so that it can be moved in the spatial direction y with a second rail 30. The second rail 30 extends perpendicularly to the first rail 28 in the spatial direction x. The length of the rails 28, 30 is selected in such a way that the transfer arm 26 can reach the desired stations (albeit not represented in detail here) outside the incubation device 16, for example a reaction vessel store 8 or a measuring unit 6. A gripping device 32, which comprises a gripper 34 which can be moved in the spatial direction z and with which reaction vessels can be taken and deposited, is mounted on the second rail 30 so that it can be moved in the spatial direction x. The controllable (by the drives, not represented) mobility in the spatial direction y on the rail 28 and in the spatial direction x on the rail 30 gives rise to a rectangular access region 36 of the first transfer arm 26 in the x-y plane, in which the gripper 34 can take and deposit reaction vessels. In the representation of FIG. 2, the incubation unit 22 is arranged fully, i.e., with all the reception positions 24, in the access region 36 of the first transfer arm 26.

The automatic analysis apparatus 1 is configured for parallel processing of a multiplicity of analyses. In order to increase the throughput of the automatic analysis apparatus 1, the incubation device 16 comprises a second transfer arm 38. This is formed in the same way as the first transfer arm 26, i.e., it is arranged on the first rail 28, which is arranged on a second rail 40 extending perpendicularly to the first rail 28 and is equipped with a gripping device 42 having a gripper 44. The length of the rail 40 is also selected in such a way that the transfer arm 38 can reach the desired stations (albeit not represented in detail here) outside the incubation device 16. The mobility of the second transfer arm 38 is configured in a similar way as for the first transfer arm 26; the same geometrical extent therefore leads to an exactly equally large rectangular access region 46 of the second transfer arm 38.

In order to avoid the problem that under certain circumstances a collision of the transfer arms may occur, the transfer arms 26, 38 are arranged in such a way that their respective access regions 36, 46 do not overlap. In particular, in the exemplary embodiment the transfer arms 26, 38 are arranged on the same rail 28 but separated from one another in the spatial direction y by a stopper 48. Correspondingly, the access regions 36, 46 are separated from one another in the spatial direction y. Contact of the two transfer arms 26, 38 is therefore—with a corresponding extent of the stopper 48, as provided here—geometrically prevented. In other exemplary embodiments, separation of the access regions may also be carried out, and contact of the transfer arms 26, 38 may be prevented, by mechanical limitation of the drives (not represented in detail) or on the control software side.

So that the two transfer arms 26, 38 can access the incubation unit 22, as already described the latter is configured to be movable in the y direction, i.e. horizontally, on the rails 20. More precisely, two positions for the incubation unit 22 are provided in the exemplary embodiment: the first position is represented in FIG. 2, namely in the access region 36 of the first transfer arm 26 such that all the reception positions 24 lie in the access region 36. In a similar way, a second position is provided in which all the reception positions 24 are arranged in the access region 46 of the second transfer arm 38.

On the control side, monitoring of the positions of the transfer arms 26, 38 in respect of a possible collision is now no longer necessary, which considerably simplifies the control software. As soon as a transfer arm 26, 38 needs to access the incubation unit 22, the latter is moved into the corresponding position below the accessing transfer arm 26, 38, if it is not already arranged there.

The described embodiment of an incubation device 16 therefore allows reliable operation with, at the same time, simplified driving of the incubation device 16.

LIST OF REFERENCES 1 automatic analysis apparatus
2 delivery rail
4 pipetting device
6 measuring unit
8 reaction vessel store
10 reagent store
12 data line
14 computer
16 incubation device
18 bottom
20 rail
22 incubation unit
24 reception position
26 transfer arm
28, 30 rail
32 gripping device
34 gripper
36 access region
38 transfer arm
40 rail
42 gripping device
44 gripper
46 access region
48 stopper
x, y, z spatial direction

The invention claimed is:

1. An incubation device for an automatic analysis apparatus, the incubation device comprising:
an incubation unit having a number of reception positions for reaction vessels,
a first transfer arm having a first gripping device for one or more reaction vessels, which is configured to move the first gripping device into a first access region, and
a second transfer arm having a second gripping device for one or more reaction vessels, which is configured to move the second gripping device into a second access region,
wherein the first and the second access regions do not overlap, and the incubation unit is mounted so that it is movable into a first position such that each of the reception positions lies in the first access region and is movable into a second position such that each of the reception positions lies in the second access region.

2. The incubation device as claimed in claim 1, wherein the first and the second transfer arms are restricted in their movement such that mutual contact between the first and the second transfer arms is prevented.

3. The incubation device as claimed in claim 2, further comprising a stopper configured between the first and the second transfer arms to restrict movement of the first and the second transfer arms such that mutual contact between the first and the second transfer arms is prevented.

4. The incubation device as claimed in claim 1, wherein the first and the second access regions lie in the same horizontal plane, and the incubation unit is horizontally movable.

5. The incubation device as claimed in claim 1, wherein the reception positions are thermally regulated.

6. An automatic analysis apparatus comprising a control unit executing corresponding software, and the incubation device as claimed in claim 1.

7. The automatic analysis apparatus as claimed in claim 6, further comprising a first unit for measuring a first physical property of a reaction mixture, and a second unit for measuring a second physical property of a reaction mixture.

8. The automatic analysis apparatus as claimed in claim 7, wherein the first and the second units for measuring a physical property of a reaction mixture are respectively configured to measure at least one optical property of the reaction mixture.

9. The automatic analysis apparatus as claimed in claim 8, wherein the first and the second units for measuring physical properties of a reaction mixture are selected from the group consisting of a photometer, nephelometer, turbidimeter, and luminometer.

10. A method for the automatic movement of one or more reaction vessels in an incubation device for an automatic analysis apparatus, the method comprising:
providing an incubation unit having a number of reception positions for reaction vessels,
moving a first transfer arm having a first gripping device for one or more reaction vessels such that the first gripping device is moved into a first access region,
moving a second transfer arm having a second gripping device for one or more reaction vessels such that the second gripping device is moved into a second access position, wherein the first and the second access regions do not overlap;

moving the incubation unit into a first position such that each of the reception positions lies in the first access region; and moving the incubation unit into a second position such that each of the reception positions lies in the second access region.

11. The method as claimed in claim 10 further comprising restricting movement of the first and the second transfer arms such that mutual contact between the first and the second transfer arms is prevented.

12. The method as claimed in claim 11 wherein the restricting movement of the first and the second transfer arms comprises providing a stopper between the first and the second transfer arms to restrict movement thereof to prevent mutual contact between the first and the second transfer arms.

13. The method as claimed in claim 10, wherein the first and the second access regions lie in the same horizontal plane, and the method further comprises moving the incubation unit horizontally.

\* \* \* \* \*